US012310610B2

(12) United States Patent
Ebrahimi et al.

(10) Patent No.: US 12,310,610 B2
(45) Date of Patent: May 27, 2025

(54) NASAL SUCTION INSTRUMENT WITH INTERCHANGEABLE TIP INSERT

(71) Applicant: Acclarent, Inc., Irvine, CA (US)

(72) Inventors: Babak Ebrahimi, Irvine, CA (US); Ehsan Shameli, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 284 days.

(21) Appl. No.: 17/881,751

(22) Filed: Aug. 5, 2022

(65) Prior Publication Data
US 2023/0081002 A1  Mar. 16, 2023

Related U.S. Application Data

(63) Continuation of application No. 16/676,502, filed on Nov. 7, 2019, now Pat. No. 11,439,420.

(60) Provisional application No. 62/777,799, filed on Dec. 11, 2018.

(51) Int. Cl.
*A61B 34/20* (2016.01)
*A61B 17/24* (2006.01)
*A61M 1/00* (2006.01)
*A61B 17/00* (2006.01)
*A61M 25/01* (2006.01)

(52) U.S. Cl.
CPC .............. *A61B 17/24* (2013.01); *A61B 34/20* (2016.02); *A61M 1/70* (2021.05); *A61M 1/76* (2021.05); *A61M 1/84* (2021.05); *A61B 2017/00477* (2013.01); *A61B 2017/246* (2013.01); *A61B 2034/2051* (2016.02); *A61B 2217/005* (2013.01); *A61M 25/0127* (2013.01); *A61M 2210/0681* (2013.01)

(58) Field of Classification Search
CPC .. A61B 2017/0046; A61B 2017/00477; A61B 2034/2051; A61B 2034/2072; A61B 2217/005; A61M 1/76; A61M 2210/0681
See application file for complete search history.

(56) References Cited

U.S. PATENT DOCUMENTS

| 6,728,565 | B2 * | 4/2004 | Wendlandt ............. A61B 1/015 600/407 |
| 7,720,521 | B2 | 5/2010 | Chang et al. |
| 10,561,370 | B2 | 2/2020 | Salazar et al. |
| 10,631,890 | B2 | 4/2020 | Palushi et al. |

(Continued)

OTHER PUBLICATIONS

International Search Report and Written Opinion dated Feb. 18, 2020, for International Application No. PCT/IB2019/060376, 14 pages.

(Continued)

*Primary Examiner* — Deanna K Hall
(74) *Attorney, Agent, or Firm* — Morgan, Lewis & Bockius LLP

(57) ABSTRACT

A suction instrument includes a proximal end, a distal end configured to be positioned within or adjacent to an anatomical passageway of a patient, and a suction lumen extending between the proximal and distal ends. The suction lumen is configured to provide suction at the distal end. A navigation sensor is disposed along a portion of the suction lumen and is operable to generate an electrical signal corresponding to a location of the portion within the patient. A coupling feature is disposed at the proximal end and is configured to releasably couple the proximal end with a body.

20 Claims, 12 Drawing Sheets

(56) References Cited

U.S. PATENT DOCUMENTS

| | | | |
|---|---|---|---|
| 11,439,420 B2 | 9/2022 | Ebrahimi et al. | |
| 2007/0208252 A1* | 9/2007 | Makower | A61B 6/032 606/198 |
| 2014/0364725 A1 | 12/2014 | Makower | |
| 2016/0008083 A1 | 1/2016 | Kesten et al. | |
| 2016/0310042 A1* | 10/2016 | Kesten | A61B 5/066 |
| 2018/0085174 A1 | 3/2018 | Radtke et al. | |
| 2018/0280049 A1 | 10/2018 | Algawi et al. | |
| 2018/0344978 A1 | 12/2018 | Shameli et al. | |
| 2019/0167351 A1 | 6/2019 | Salazar et al. | |
| 2019/0175282 A1 | 6/2019 | Akbarian et al. | |
| 2019/0192176 A1 | 6/2019 | Palushi et al. | |
| 2019/0374129 A1 | 12/2019 | Palushi et al. | |

OTHER PUBLICATIONS

Japanese Notification of Reasons for Refusal dated Jul. 25, 2023, for Application No. 2021-533212, 7 pages.

Japanese Notification of Reasons for Refusal dated Jan. 23, 2024, for Application No. 2021-533212, 2 pages. ...........

Provisional U.S. Appl. No. 62/658,688, entitled "Curette with Navigation Sensor," filed Mar. 17, 2018.

Provisional U.S. Appl. No. 62/765,168, entitled "Endoscope with Anatomy Elevation Assembly," filed Aug. 17, 2018.

Provisional U.S. Appl. No. 62/741,594, entitled "Hollow Tube Surgical Instrument with Single Axis Sensor," filed Oct. 5, 2018.

Provisional U.S. Appl. No. 62/741,614, entitled "Dilation Instrument with Malleable Guide and Dilation Catheter with Integral Position Sensor," filed Oct. 5, 2018.

Provisional U.S. Appl. No. 62/741,778, entitled "Pointer Instrument with Malleable Shaft and Integral Position Sensor," filed Oct. 5, 2018.

* cited by examiner

NASAL SUCTION INSTRUMENT WITH INTERCHANGEABLE TIP INSERT

PRIORITY

This application is a continuation of U.S. patent application Ser. No. 16/676,502, filed Nov. 7, 2019, issued as U.S. Pat. No. 11,439,420 on Sep. 13, 2022, entitled "Nasal Suction Instrument with Interchangeable Tip Insert," which claims the benefit of U.S. Prov. Pat. App. No. 62/777,799, filed Dec. 11, 2018, the disclosure of which is incorporated by reference herein.

BACKGROUND

In some instances, it may be desirable to operate within or adjacent to an anatomical passageway of a patient, such as performing an incision of mucosa, removal of bone, or dilation of an anatomical passageway. Such operations may occur within anatomical passageways such as ostia of paranasal sinuses (e.g., to treat sinusitis), the larynx, the Eustachian tube, or other passageways within the ear, nose, or throat, etc. In addition to the above described operations, or similar operations, it may be desirable to apply suction and/or irrigation within or adjacent to an anatomical passageway before, during, or after the above described operations, or similar operations. One method of applying suction within or adjacent to an anatomical passageway of a patient involves obtaining a suction device having an elongate shaft defining a lumen terminating at an open distal end of the elongated shaft, where the lumen is in fluid communication with an external suction source. An operator may then insert the distal end of the elongate shaft within the nostril or mouth of a patient toward a desired location within the patient. With the distal end of the elongate shaft inserted within the patient, an operator may manipulate the suction device and/or suction source in order to remove extraneous and/or undesired matter near or within an anatomical passageway of a patient. Applying suction and/or irrigation during an operation may be beneficial for multiple purposes as will be apparent to those skilled in the art.

Image-guided surgery (IGS) is a technique in which a computer is used to obtain a real-time correlation of the location of an instrument that has been inserted into a patient's body to a set of preoperatively obtained images so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a system display device (e.g., a video monitor) along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, California; systems available from Surgical Navigation Technologies, Inc., of Louisville, Colorado; and systems available from Calypso Medical Technologies, Inc., of Seattle, Washington.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
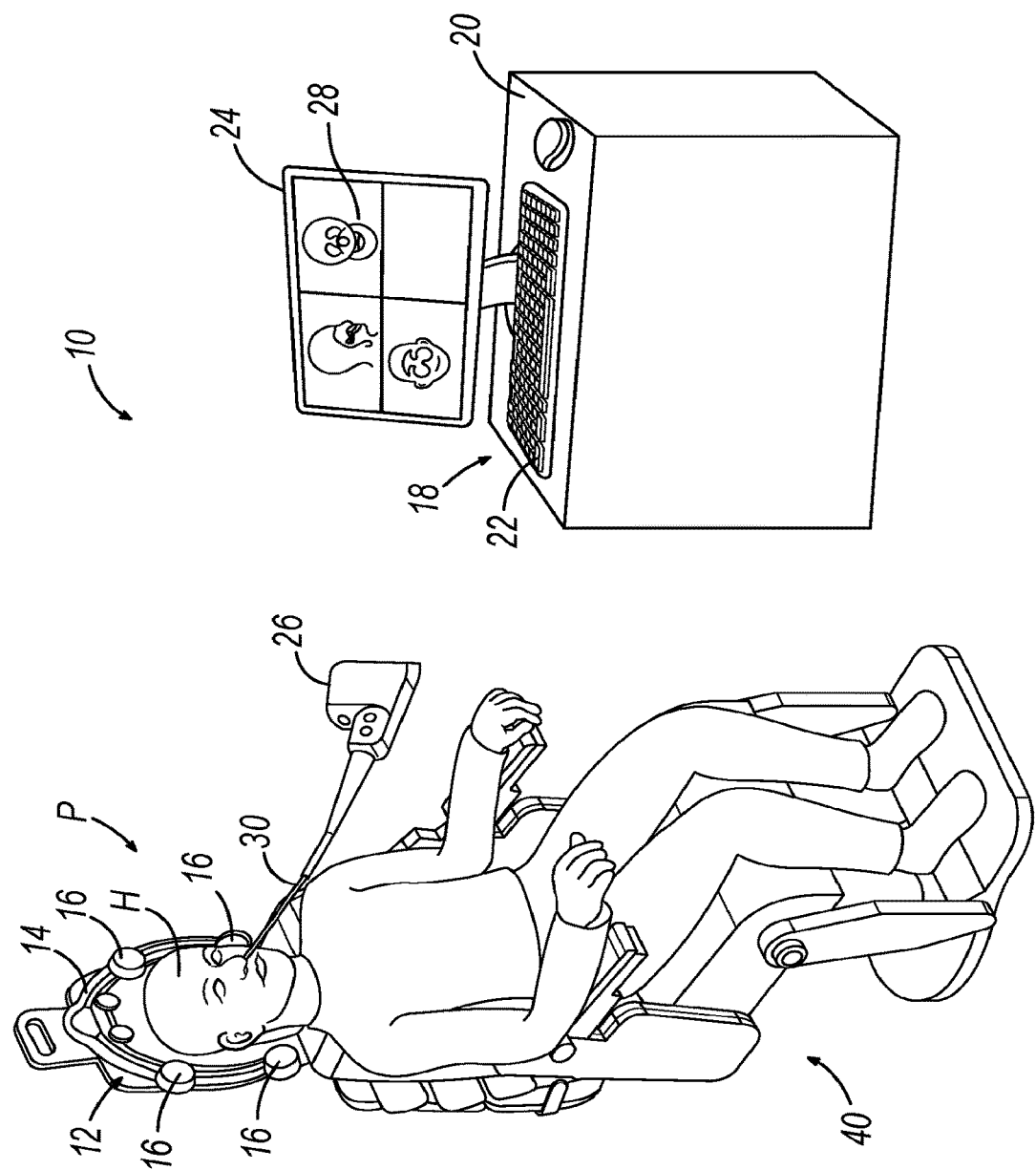
FIG. 1 depicts a schematic view of an exemplary sinus surgery navigation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges are intended to encompass the exact value(s) referenced as well as a suitable dimensional tolerance that allows the part or collection of components to function for its intended purpose as described herein.

I. Exemplary Image Guided Surgery Navigation System

When performing a medical procedure within a head (H) of a patient (P), it may be desirable to have information regarding the position of an instrument within the patient's head (H), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (12), which comprises magnetic field generators (16) that are integrated into a horseshoe-shaped frame (14). Field generators (16) are operable to generate alternating magnetic fields of different frequencies around the head (H) of the patient (P). A navigation guidewire (30) is inserted into the head (H) of the patient (P) in this example. Navigation guidewire (30) may be a standalone device or may be positioned on an end effector or other location of a medical instrument such as a surgical cutting instrument or dilation instrument. In the present example, frame (14) is mounted to a chair (40), with the patient (P) being seated in the chair (40) such that frame (14) is located adjacent to the head (H) of the patient (P). By way of example only, chair (40) and/or field generator assembly (12) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (10) of the present example further comprises a processor (18), which controls field generators (16) and other elements of IGS navigation system (10). For instance, processor (18) is operable to drive field generators (16) to generate alternating electromagnetic fields; and process signals from navigation guidewire (30) to determine the location of a sensor in navigation guidewire (30) within the head (H) of the patient (P). Processor (18) comprises a processing unit communicating with one or more memories. Processor (18) of the present example is mounted in a console (20), which comprises operating controls (22) that include a keypad and/or a pointing device such as a mouse or trackball. A physician uses operating controls (22) to interact with processor (18) while performing the surgical procedure.

Navigation guidewire (30) includes a sensor (not shown) that is responsive to positioning within the alternating magnetic fields generated by field generators (16). A coupling unit (26) is secured to the proximal end of navigation guidewire (30) and is configured to provide communication of data and other signals between console (20) and navigation guidewire (30). Coupling unit (26) may provide wired or wireless communication of data and other signals between console (20) and navigation guidewire (30).

In the present example, the sensor of navigation guidewire (30) comprises at least one electrically conductive coil at the distal end of navigation guidewire (30). When such a coil is positioned within an alternating electromagnetic field generated by field generators (16), the alternating magnetic field may generate electrical current in the coil, and this electrical current may be communicated proximally along the electrical conduit(s) in navigation guidewire (30) and further to processor (18) via coupling unit (26). This phenomenon may enable IGS navigation system (10) to determine the location of the distal end of navigation guidewire (30) or other medical instrument (e.g., dilation instrument, surgical cutting instrument, etc.) within a three-dimensional space (i.e., within the head (H) of the patient (P), etc.). To accomplish this, processor (18) executes an algorithm to calculate location coordinates of the distal end of navigation guidewire (30) from the position related signals of the coil(s) in navigation guidewire (30). While the position sensor is located in guidewire (30) in this example, such a position sensor may be integrated into various other kinds of instruments, including those described in greater detail below.

Processor (18) uses software stored in a memory of processor (18) to calibrate and operate IGS navigation system (10). Such operation includes driving field generators (16), processing data from navigation guidewire (30), processing data from operating controls (22), and a driving display screen (24). In some implementations, operation may also include monitoring and enforcement of one or more safety features or functions of IGS navigation system (10). Processor (18) is further operable to provide video in real time via display screen (24), showing the position of the distal end of navigation guidewire (30) in relation to a video camera image of the patient's head (H), a CT scan image of the patient's head (H), and/or a computer generated three-dimensional model of the anatomy within and adjacent to the patient's nasal cavity. Display screen (24) may display such images (28) simultaneously and/or superimposed on each other during the surgical procedure. Such displayed images (28) may also include graphical representations of instruments that are inserted in the patient's head (H), such as navigation guidewire (30), such that the operator may view the virtual rendering of the instrument at its actual location in real time. By way of example only, display screen (24) may provide images (28) in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (24).

The images (28) provided through display screen (24) may help guide the operator in maneuvering and otherwise manipulating instruments within the patient's head (H) when such instruments incorporate navigation guidewire (30). It should also be understood that other components of a surgical instrument and other kinds of surgical instruments, as described below, may incorporate a sensor like the sensor of navigation guidewire (30).

II. Exemplary Navigable Suction Instrument

Various surgical procedures may warrant the use of a suction instrument in order to clear fluids and/or debris from the surgical field and/or from other sites within a patient. For instance, suction may be desirable in FESS procedures, sinuplasty procedures, and/or in various other ENT procedures. Furthermore, in some instances, it may be desirable to provide image guided navigation capabilities to such a suction instrument.

Figure 2:
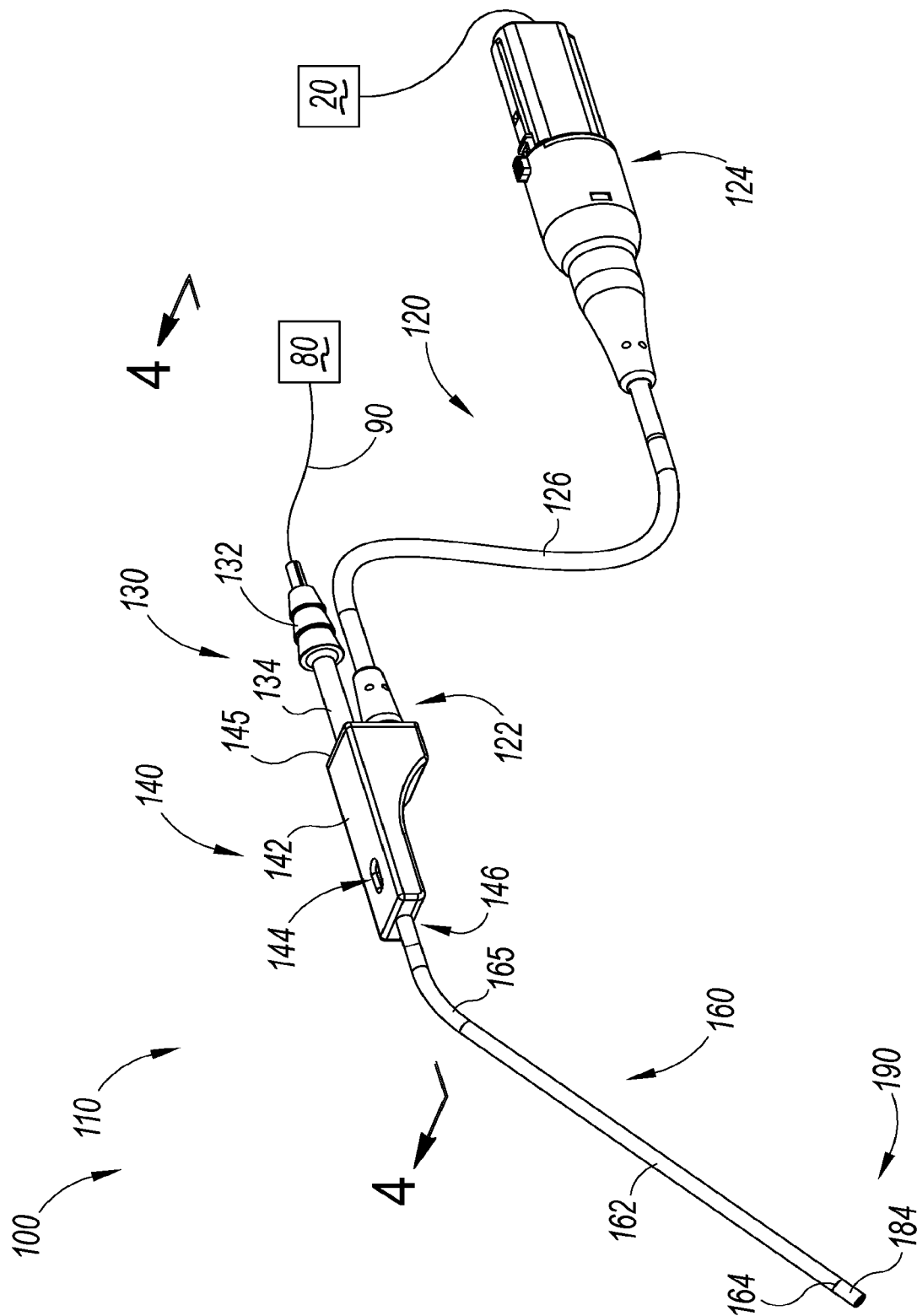
FIG. 2 depicts a perspective view of an exemplary assembly having a suction instrument and a coupling unit for coupling the suction instrument with the navigation system of FIG. 1.

FIG. 2 shows an exemplary suction instrument assembly (100) operable to provide suction during surgical procedures, and which is configured for use with IGS navigation system (10) described above. Suction instrument assembly (100) includes a suction instrument (110) that is fluidly coupled with a suction source (80) via a suction conduit (90). Suction source (80) may comprise a vacuum pump and a fluid reservoir, among other components readily apparent to persons of ordinary skill in the art, and is configured to provide enough suction at a surgical site to pull excess fluid and/or debris proximally through suction instrument (110).

Figure 3:
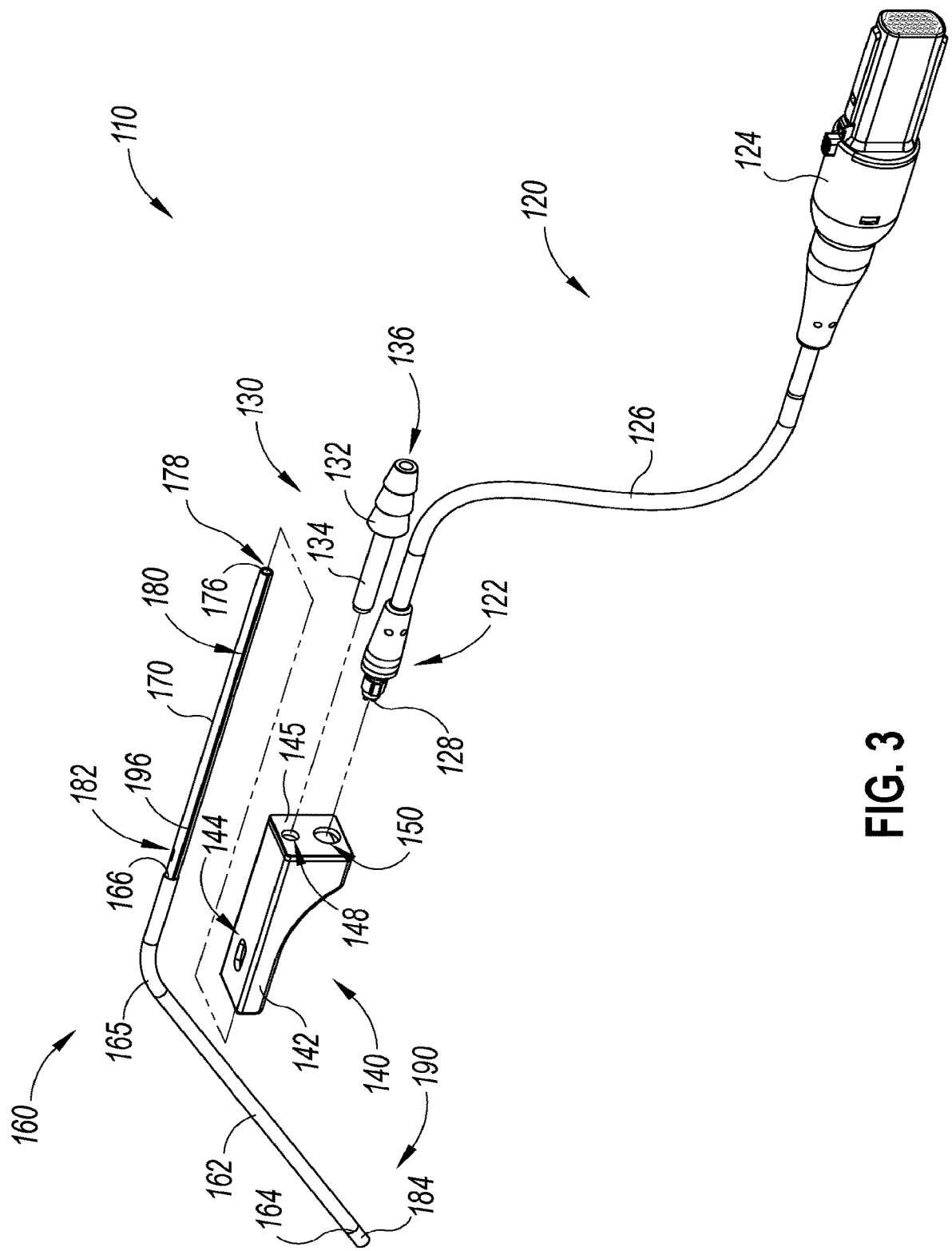
FIG. 3 depicts an exploded perspective view of the suction instrument of FIG. 2.

As best seen in FIGS. 2 and 3, suction instrument (110) includes a coupling unit (120), a proximal suction conduit port (130), a grip portion (or "handle assembly") (140), and an elongate cannula assembly (160). A distal end of cannula assembly (160) is configured to be inserted, transnasally or otherwise, within or adjacent to a nasal cavity of a patient (or elsewhere within a patient) to provide suction at a selected surgical site. Cannula assembly (160) includes a sensor assembly (190) mounted at a distal end thereof. As described below, sensor assembly (190) includes a navigation sensor operable to communicate signals to console (20) of IGS navigation system (10) via coupling unit (120). Based on these signals, processor (18) may execute an algorithm to determine a 3-dimensional spatial location of the distal end of cannula assembly (160) relative to the anatomy of patient (P).

Coupling unit (120) includes a sensor coupling (122), a console coupling (124), and a cable (126) connecting and establishing communication between sensor coupling (122) and console coupling (124). Sensor coupling (122) includes prongs (128) that are housed within a proximal cavity (156) of grip portion (140). Console coupling (124) is configured to couple with console (20), and sensor coupling (122) is configured to couple with sensor assembly (190) of suction instrument (110), such that sensor assembly (190) is in communication with console (20). Console coupling (124) may be in wired or wireless communication with console (20), similar to coupling unit (26) described above. Additionally, coupling unit (120) may be configured to communicate data or other signals uni-directionally or bi-directionally between suction instrument (110) and console (20).

Proximal suction conduit port (130) includes a proximal barbed configuration (132), a distal shaft (134), and an internal pathway (136). Proximal barbed configuration (132) is configured to provide a secure fit with conduit (90) such that pathway (136) and the interior of conduit (90) are in fluid communication with each other.

Figure 4:
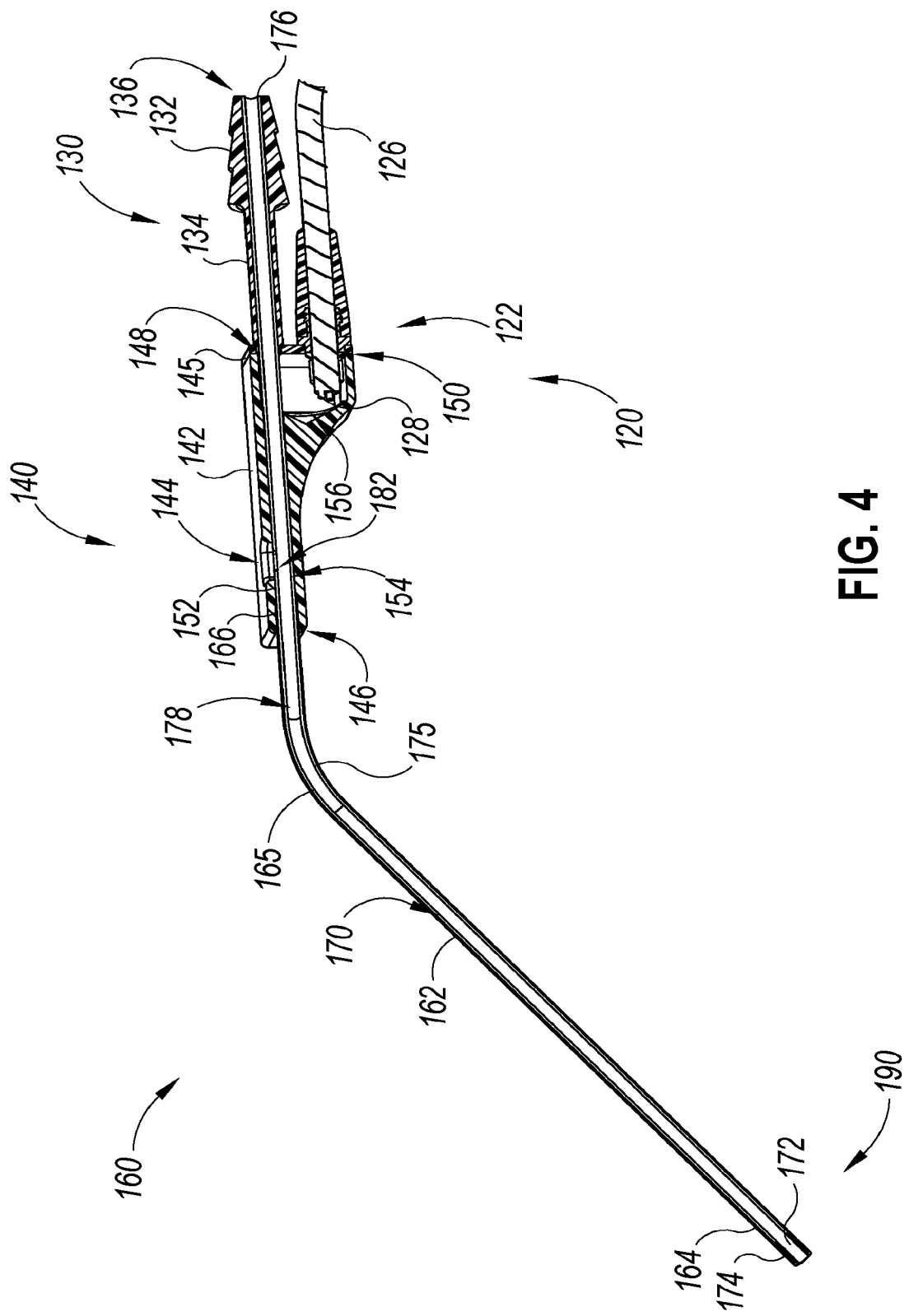
FIG. 4 depicts a cross-sectional perspective view of the suction instrument of FIG. 2, taken along section line 4-4 of FIG. 2.
Figure 5:
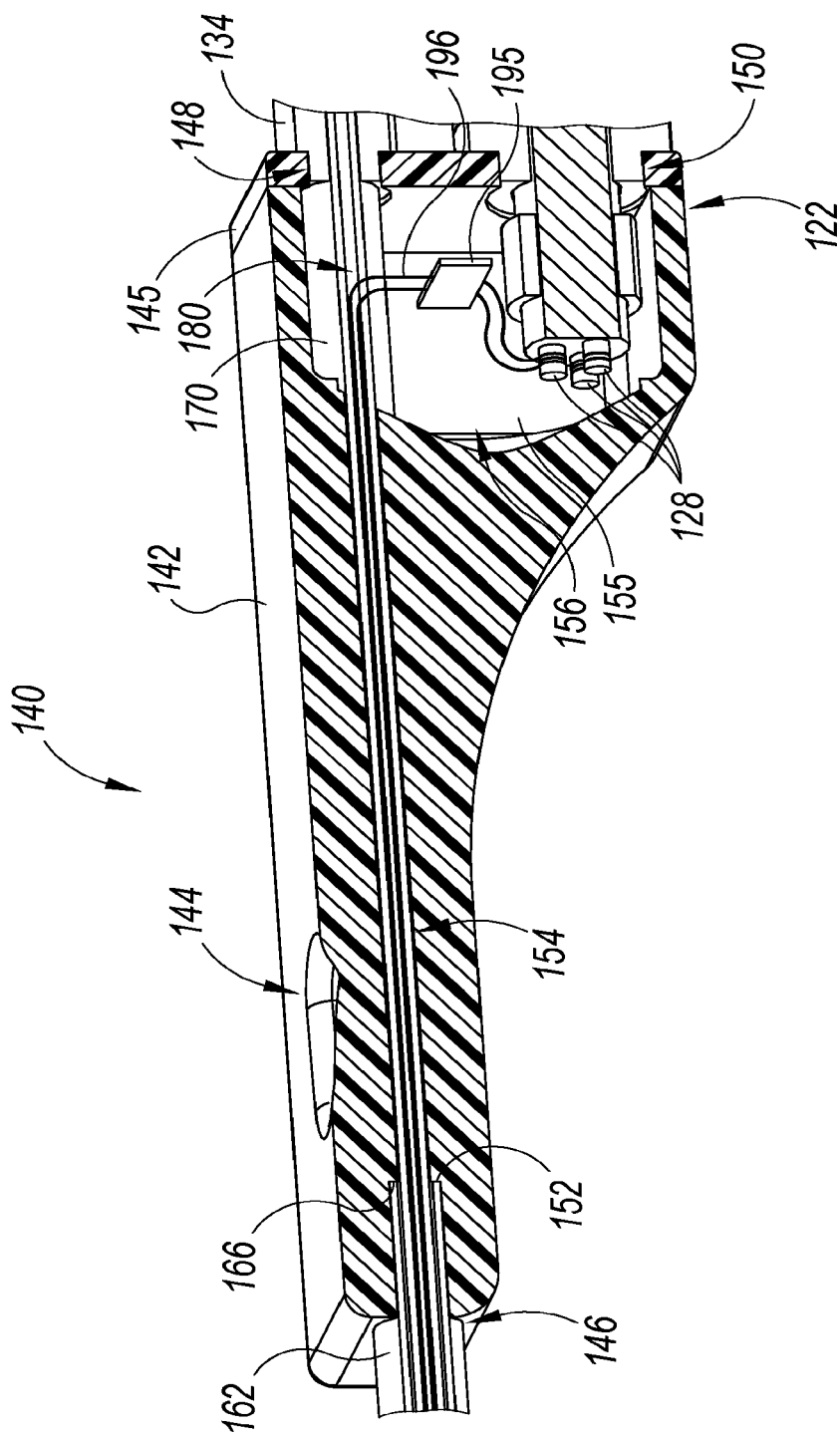
FIG. 5 depicts a cross-sectional perspective view of a handle assembly of the suction instrument of FIG. 2.

As shown in FIGS. 2-5, grip portion (140) includes a body (142) and a proximal cap (145). Body (142) may be grasped by an operator such that the operator may manipulate and control suction instrument (110). Body (142) defines a first vent opening (144), a distal opening (146), proximal cavity (156), and a pathway (154) that extends from distal opening (146) into proximal cavity (156). Proximal cap (145) attaches to a proximal portion of body (142) and closes proximal cavity (156). Proximal cap (145) includes a first proximal opening (148) that receives shaft (134) of proximal suction conduit port (130), and a second proximal opening (150) that receives sensor coupling (122) of coupling unit (120). As shown in FIG. 5, pathway (154) includes a distally presented shoulder (152) configured to abut an open proximal end (166) of an external sheath (162) of cannula assembly (160) when inserted proximally through distal opening (146) during assembly.

Elongate cannula assembly (160) includes an external sheath (162), an interior suction tube (170), a sensor assembly (190), and a distal cap (184) covering sensor assembly (190). External sheath (162) extends from an open distal end (164) to an open proximal end (166), with a bent portion (165) located therebetween. External sheath (162) defines a hollow interior that houses a portion of interior suction tube (170) as well as a portion of a communication wire (196) extending within and along a guided path (180) defined by interior suction tube (170).

Interior suction tube (170) extends from an open distal end (174) to an open proximal end (176), with a bent portion (175) located therebetween. As shown in FIG. 4, interior suction tube (170) includes a narrowed distal portion (172) that extends distally of open distal end (164) of external sheath (162) and through sensor assembly (190), such that sensor assembly (190) is fixed to narrowed distal portion (172). As shown in FIG. 3, interior suction tube (170) defines a guided path (180) that houses communication wire (196) extending proximally from sensor assembly (190), in cooperation with external sheath (162). Suction tube (170) and external sheath (162) may be rigid and configured to maintain the bend of bent regions (165, 175) without buckling during insertion into a patient's nasal cavity.

As shown in FIG. 4, interior suction tube (170) defines a suction lumen (178) that extends from open distal end (174) to open proximal end (176). A proximal portion of interior suction tube (170) is received through distal opening (146) of grip portion body (142) and extends proximally into pathway (136) of suction conduit port (130), such that suction lumen (178) is configured to fluidly couple with suction source (80) via suction conduit (90). As shown in FIGS. 3 and 4, first vent opening (144) of grip portion (140) fluidly communicates with suction lumen (178) through a second vent opening (182) formed in suction tube (170). During operation, an operator may grasp grip portion (140) and selectively close first vent opening (144) to communicate suction from suction source (80) to suction lumen (178). As shown, first vent opening (144) may be formed with a teardrop shape (or some other elongate shape) to enable the operator to selectively vary the amount of suction communicated from suction source (80) to suction lumen (178) based on the longitudinal position of the operator's thumb (or other finger) on first vent opening (144).

In some instances, suction source (80) remains in a constantly activated state throughout a surgical procedure. In such instances, the operator may leave first vent opening (144) uncovered while positioning open distal end (174) of instrument (110) within the patient such that suction source (80) draws suction through vent openings (144, 182) rather than through open distal end (174). When the operator wishes to apply suction to a target surgical site within the patient via open distal end (174), the operator at least partially covers vent opening (144) with a thumb, finger, or other object, so that suction is then communicated from suction source (80) to open distal end (174).

Sensor assembly (190) of cannula assembly (160) may include an annular navigation sensor (not shown) in accordance with the teachings of U.S. patent application Ser. No. 15/964,886, entitled "Navigable Suction Instrument With Coaxial Annular Sensor," filed Apr. 27, 2018, issued as U.S. Pat. No. 11,253,677 on Feb. 22, 2022, the disclosure of which is incorporated by reference herein. The navigation sensor may include one or more electrically conductive members such as coils, layers of wire windings, etc. in which an electrical current is induced in response to presence of sensor assembly (190) within an electromagnetic field generated by field generators (16) of IGS navigation system (10). One or more sensor wires (not shown) extend proximally from sensor assembly (190) through cannula assembly (160) and couple with communication wire (196), which extends along guided path (180) into proximal cavity (156) of grip portion (140), as shown in FIG. 5. Communication wire (196) is coupled with a PCB board (195) that in turn couples with prongs (128) of sensor coupling (122). As described above, coupling unit (120) is configured to communicate with console (20) of IGS navigation system (10).

Electrical currents induced within the navigation sensor of sensor assembly (190) are transmitted as electrical signals proximally through the sensor wires to communication wire (196), through PCB board (195), and to coupling unit (120), which communicates the signals to console (20) of IGS navigation system (10). Processor (18) then executes an algorithm to calculate 3-dimensional location coordinates of the navigation sensor based on the received electrical signals. Because sensor assembly (190) is fixed at the distal end (174) of elongate cannula assembly (160), IGS navigation system (10) may thus calculate, track, and display the location of at least the distal end within the patient (P) in real time during a surgical procedure. While tracking the location of cannula assembly (160) within patient (P), an operator may selectively apply suction at any suitable time in accordance with the teachings above. It will be appreciated that suction instrument assembly (100) may be further configured and operable in accordance with one or more teachings of U.S. patent application Ser. No. 15/964,886, issued as U.S. Pat. No. 11,253,677 on Feb. 22, 2022, incorporated by reference above.

III. Exemplary Navigable Suction Instruments Having Detachable Suction Tips

As described above in connection with suction instrument (110), grip portion (140) and cannula assembly (160) are permanently coupled mechanically and electrically during assembly so as to define a single unit that is manipulated by an operator. In some instances, it may be desirable to alternatively configure grip portion (140) and cannula assembly (160) such that these components are modular and may be selectively detached from one another by an operator when desired, for example during a surgical procedure. For instance, it may be desirable to use different cannula assemblies (160) with different bend angles at respective bent portions (165), to facilitate access to different anatomical regions during a surgical procedure.

Moreover, providing a selective coupling between grip portion (140) and cannula assembly (160) may facilitate a disposable/reusable dichotomy between grip portion (140) and cannula assembly (160). For instance, a modular grip portion (140) may be subject to no re-uses or a certain first limited number of re-uses; while a modular cannula assembly (160) may be subject to no re-uses or a certain second limited number of re-uses. The following description provides merely illustrative examples of how suction instrument (110) may be modified to provide a selective coupling between a modular grip portion (140) and a modular cannula assembly (160).

A. Navigable Suction Instrument Having Suction Attachment with Connector Block

Figure 6A:
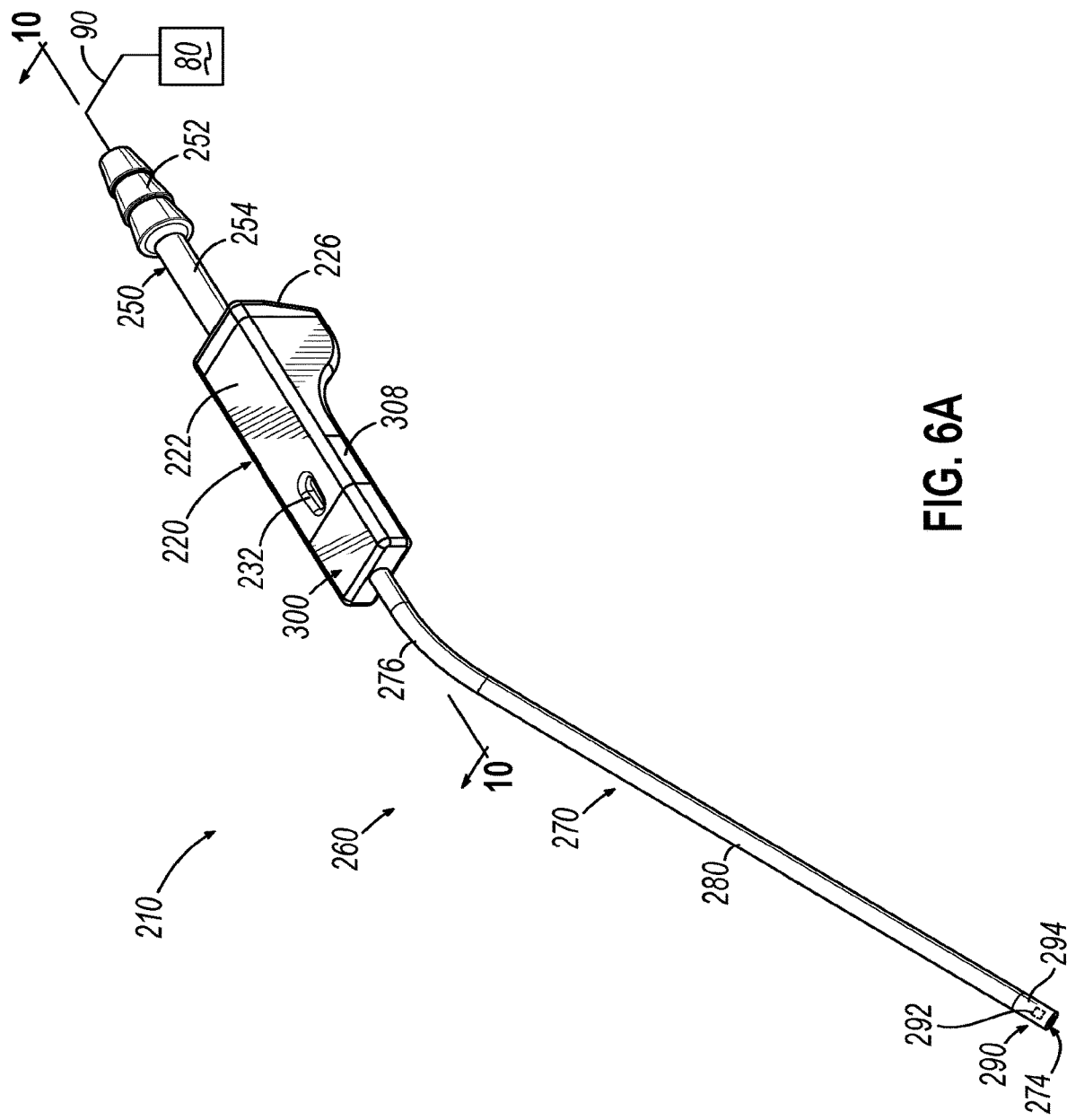
FIG. 6A depicts a perspective view of another exemplary suction instrument suitable for use with the navigation system of FIG. 1, showing a distal suction attachment coupled with a proximal handle assembly.
Figure 6B:
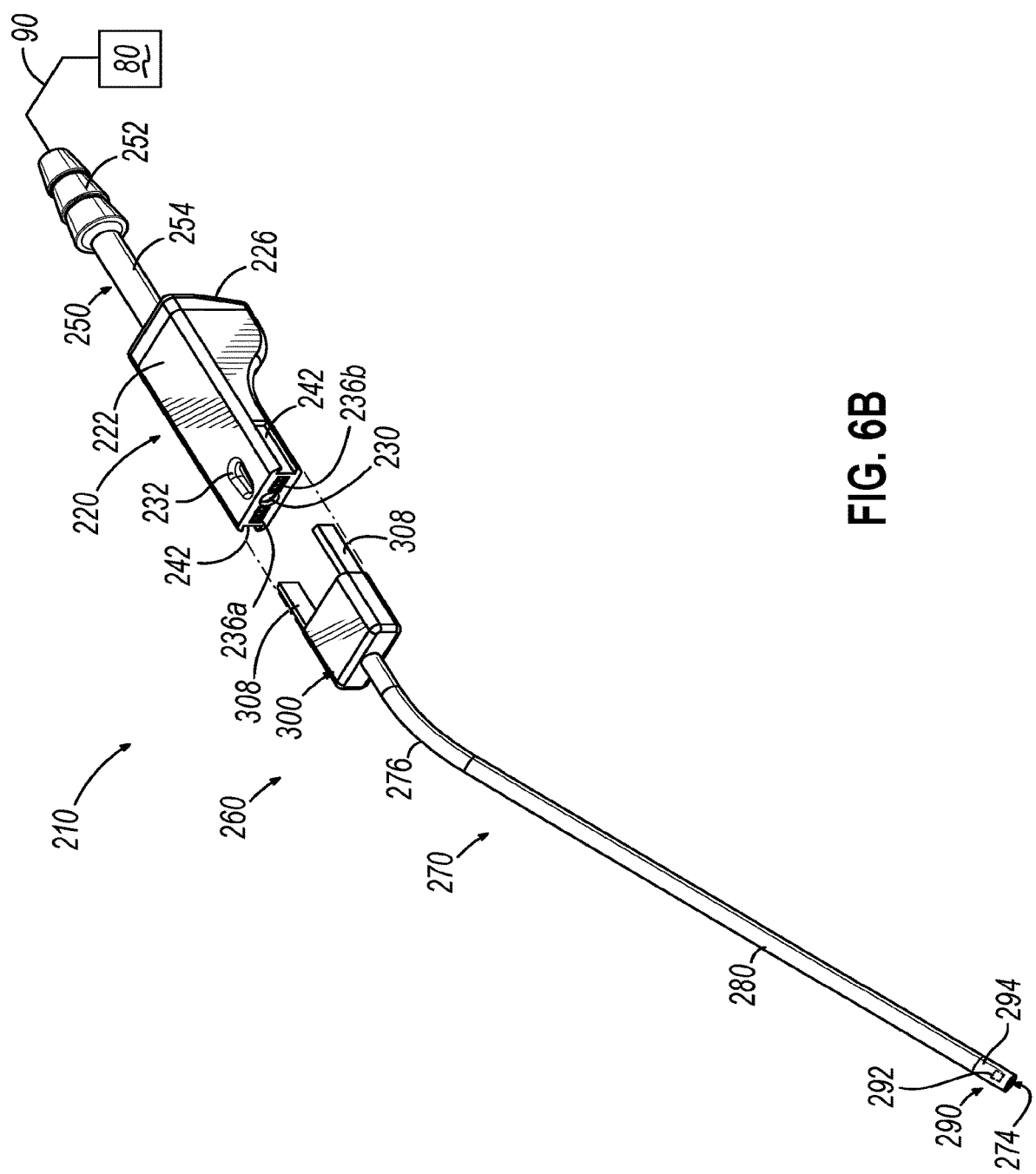
FIG. 6B depicts another perspective view of the suction instrument of FIG. 6A, showing the distal suction attachment decoupled from the proximal handle assembly.
Figure 7:
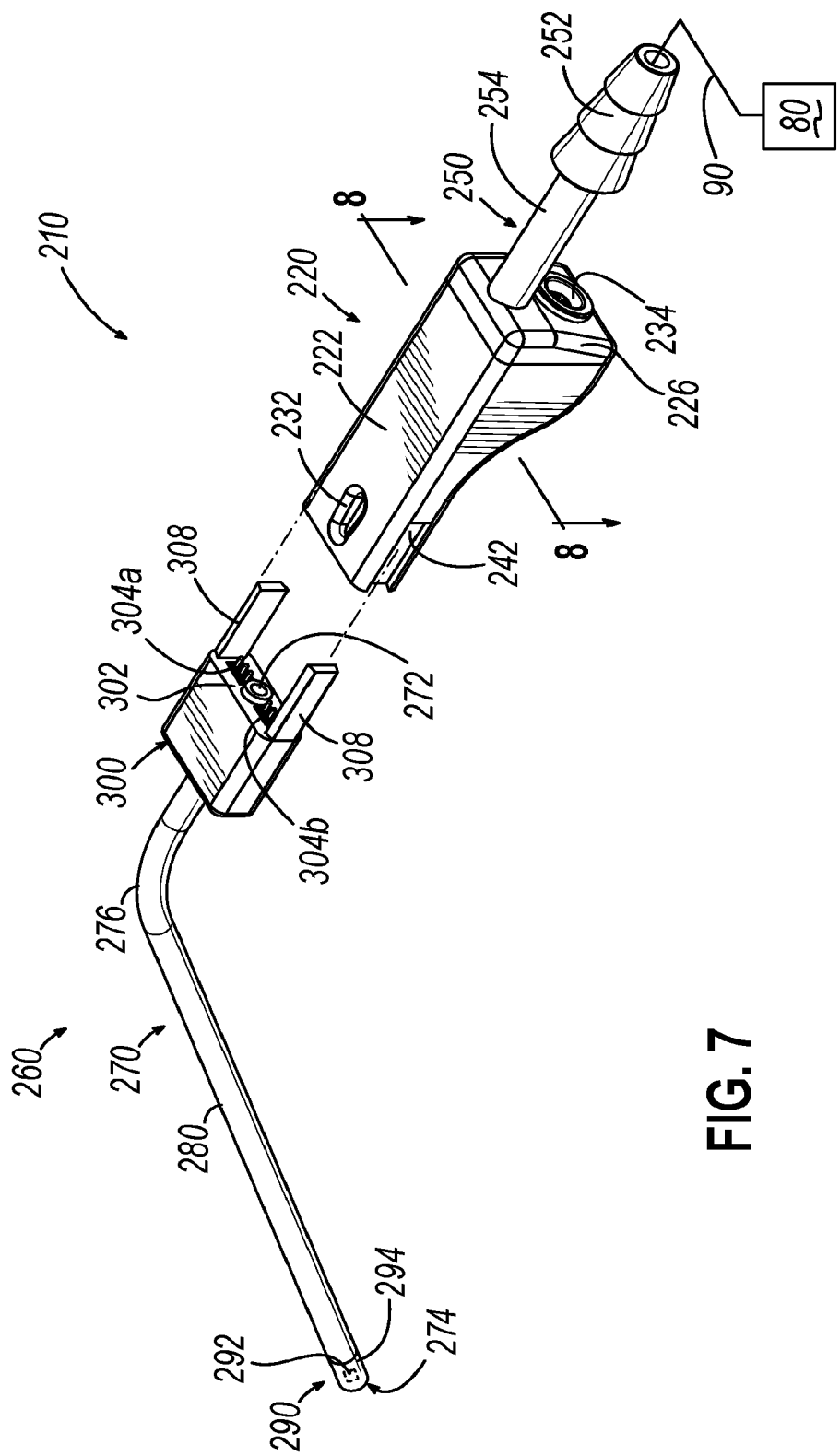
FIG. 7 depicts another perspective view of the suction instrument of FIG. 6A, showing the distal suction attachment decoupled from the proximal handle assembly.

FIG. 6A-7 show an exemplary alternative suction instrument (210) having a grip portion (or "handle assembly")

(220) and a suction attachment (260) configured to releasably couple with handle assembly (220), as described in greater detail below. It will be appreciated that suction instrument (210) is similar to suction instrument (110) described above, except as otherwise described below. As shown in FIGS. 6A-8, handle assembly (220) includes a body (222) that defines an interior cavity (224), and a proximal cap (226) coupled to a proximal end of body (222). As shown best in FIG. 8, an inner tube structure (228) extends longitudinally through interior cavity (224) to define a suction passage (230) similar to pathway (154) of handle assembly (140) described above. Inner tube structure (228) is suitably arranged within handle assembly body (222) such that a distal end of suction passage (230) opens to a distal end of body (222), and a proximal end of suction passage (230) opens to a proximal end of body (222) through proximal cap (226). As shown in FIGS. 6A-7, a vent opening (232) extends through an upper surface of body (222) and opens to suction passage (230). Vent opening (232) is suitably shaped and configured to be selectively covered by an operator to communicate suction from suction source (80) to a suction lumen (284) of suction attachment (260) in a manner similar to that described above in connection with suction instrument (110).

Figure 8:
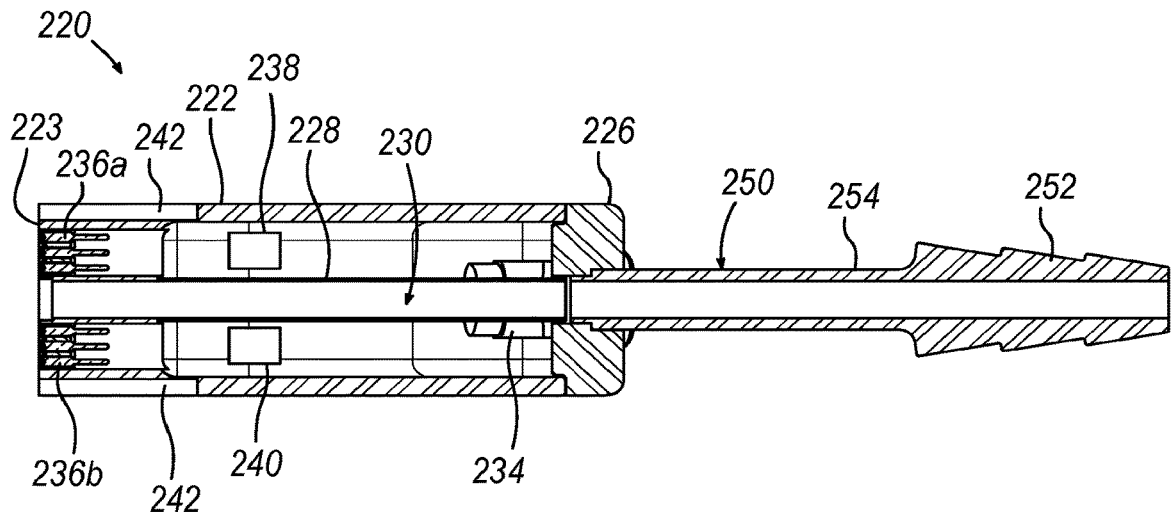
FIG. 8 depicts a top cross-sectional view of the handle assembly of the suction instrument of FIG. 6A, taken along section line 8-8 in FIG. 7.
Figure 10:
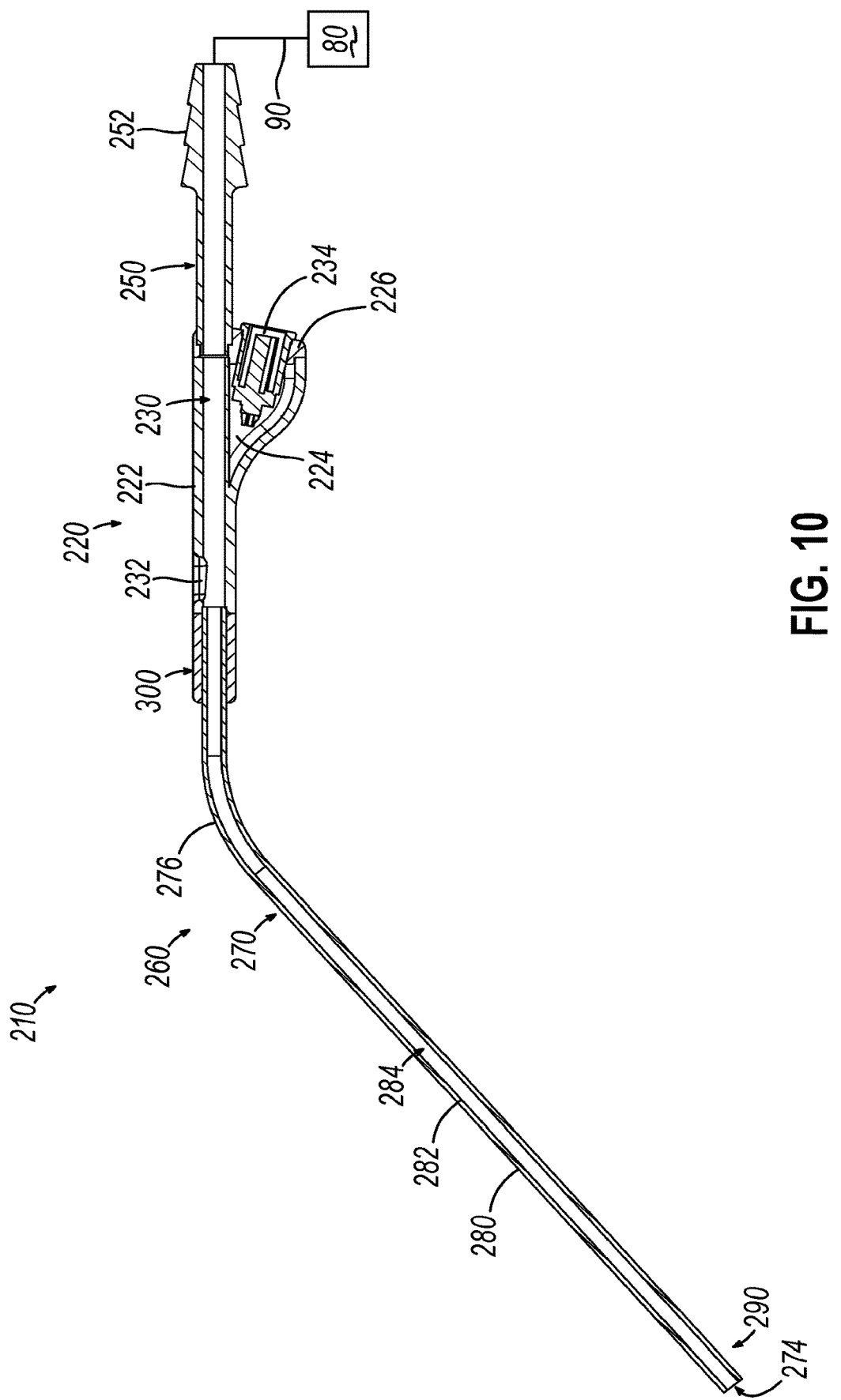
FIG. 10 depicts a side cross-sectional view of the suction instrument of FIG. 6A, showing the distal suction attachment coupled to the proximal handle assembly, taken along section line 10-10 in FIG. 6A.

As shown best in FIGS. 7, 8, and 10, a proximal end of handle assembly body (222) houses a coupling connector (234) within a proximal portion of interior cavity (224), such that coupling connector (234) is accessible through proximal cap (226). Coupling connector (234) is configured to releasably receive and electrically couple with coupling unit (120) described above, or a similar coupling device, such that handle assembly (220) may be placed in communication with console (20) of IGS navigation system (10). In some versions, coupling connector (234) may comprise a LEMO® connector. It should be understood that coupling connector (234) is merely optional, and that in some alternative versions the distal end of coupling unit (120) may be integrated into handle assembly (220).

As shown best in FIGS. 6B and 8, a distal end of handle assembly body (222) houses a pair of electrical connectors (236a, 236b) within a distal portion of interior cavity (224). Electrical connectors (236a, 236b) are exposed through a distal face (223) of body (222) and are positioned on either lateral side of the open distal end of suction passage (230). Each electrical connector (236a, 236b) is configured to electrically couple with a respective electrical connector (304a, 304b) of suction attachment (260) when suction attachment (260) is coupled with handle assembly (220), as described in greater detail below. As shown in FIG. 8, body (222) additionally houses a PCB board (238) (shown schematically) within cavity (224), which may be similar to PCB board (195) described above. One or both of electrical connectors (236a, 236b) are electrically coupled with the PCB board (238), which in turn is electrically coupled with coupling connector (234).

Handle assembly body (222) of the present example additionally houses an electrically erasable programmable read-only memory (EEPROM) (240) (shown schematically) within interior cavity (224). Handle EEPROM (240) is operable to store data relating to handle assembly (220), such as a serial number and/or past usage of handle assembly (220). Handle EEPROM (240) is electrically coupled with PCB board (238), which in turn is configured to communicate with an external processor, such as processor (18) of navigation system (10), via electrical connector (234) and coupling unit (120).

Handle assembly (220) of the present example further includes a first coupling feature that comprises a pair of recessed channels (242) formed in opposed lateral sides of a distal portion of handle assembly body (222). Recessed channels (242) are configured to releasably receive a second coupling feature (308) of suction attachment (260) when suction attachment (260) is coupled to handle assembly (220). As described in greater detail below, this engagement of coupling features (242, 308) promotes alignment of handle assembly electrical connectors (236a, 236b) with suction attachment electrical connectors (304a, 304b), and alignment of a suction lumen (284) of cannula assembly (270) with suction passage (230) of handle assembly (220).

A suction conduit port (250) similar to suction conduit port (130) described above extends proximally from handle assembly body (222). Suction conduit port (250) includes a proximal barbed portion (252) and a distal shaft portion (254). Proximal barbed portion (252) is configured to couple with suction conduit (90), and distal shaft portion (254) inserts into an upper opening formed in proximal cap (226) of handle assembly (220) such that an inner passage of suction conduit port (250) fluidly communicates with suction passage (230) of handle assembly (220). Accordingly, suction conduit port (250) is configured to communicate suction from suction source (80) and suction conduit (90) to suction passage (230) of handle assembly (220).

Figure 9:
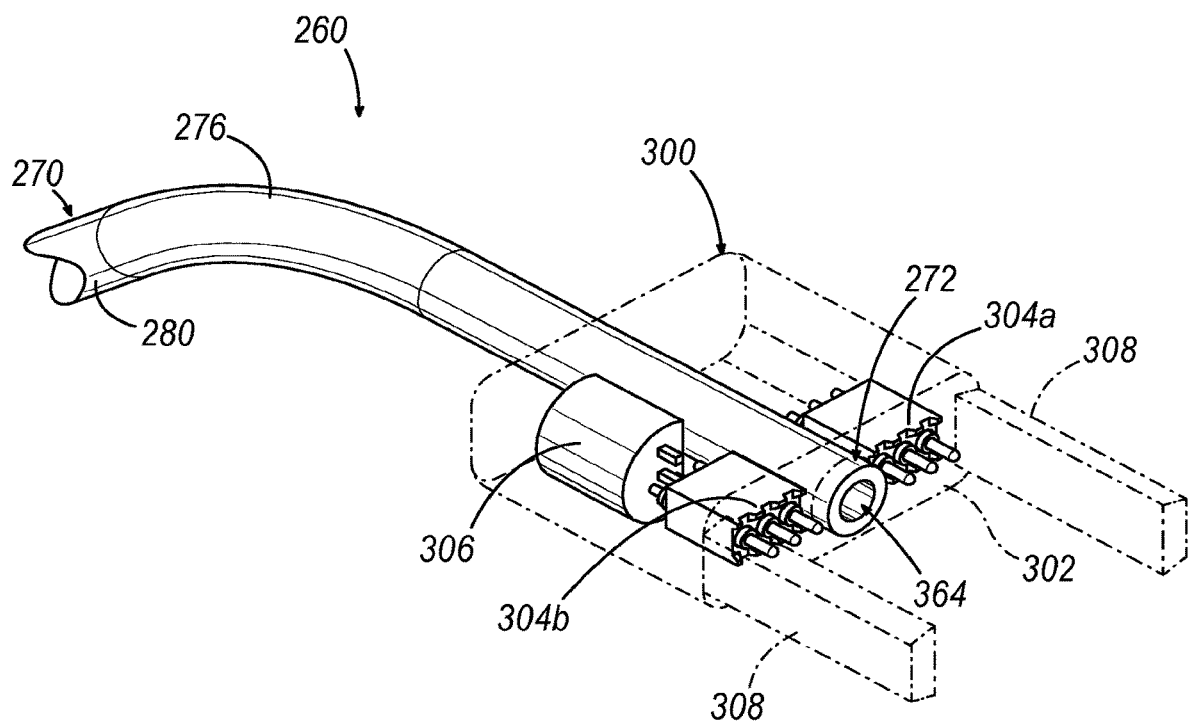
FIG. 9 depicts a perspective view of a proximal end of the distal suction attachment of the suction instrument of FIG. 6A, with a connector block of the suction attachment shown transparently to reveal features arranged within the connector block.

Suction attachment (260) of suction instrument (210) includes an elongate cannula assembly (270) and a connector block (300) affixed to a proximal portion of cannula assembly (270). Cannula assembly (270) extends between an open proximal end (272) and an open distal end (274); and has a bent portion (276) located therebetween. Cannula assembly (270) is similar to cannula assembly (160) described above in that cannula assembly (270) includes an external sheath (280), an interior suction tube (282) defining a suction lumen (284), a sensor assembly (290) mounted at open distal end (274), and a distal cap (294) that circumferentially encloses sensor assembly (290). External sheath (280) and interior suction tube (282) comprise hollow interiors and extend between open proximal end (272) and open distal end (274) of cannula assembly (270). Furthermore, external sheath (280) and/or interior suction tube (282) may be provided with a rigid construction that maintains the bend angle of bent portion (276) without buckling during insertion of cannula assembly (270) into a patient's nasal cavity. Unlike suction tube (170) of suction instrument (110), suction tube (282) of the present example is not configured to extend through a full length of handle assembly body (222) and into suction conduit port (250) upon coupling of suction attachment (260) to handle assembly (220). As shown in FIGS. 9 and 10, suction tube (282) terminates just proximally of a proximal face (302) of connector block (300) and is configured to insert into only a distal portion of suction passage (230) of handle assembly body (222) upon assembly of suction instrument (210). Such a configuration advantageously minimizes a length of the proximal portion of cannula assembly (270).

Sensor assembly (290) of cannula assembly (270) may include components similar to those of sensor assembly (190) described above, including a navigation sensor (292). Navigation sensor (292) is operable to communicate electrical signals to console (20) of IGS navigation system (10) so that processor (18) may execute an algorithm to determine a 3-dimensional spatial location of navigation sensor (292), and thus distal end (274) of cannula assembly (270), relative to the anatomy of patient (P). Navigation sensor (292) may include one or more electrically conductive members such as coils, layers of wire windings, etc. in which an electrical current is induced in response to presence of navigation sensor (292) within an electromagnetic field generated by field generators (16) of IGS navigation system (10). By way of example only, navigation sensor (292) may comprise an annular sensor of the type disclosed in U.S. patent application Ser. No. 15/964,886, issued as U.S. Pat. No. 11,253,677 on Feb. 22, 2022, incorporated by reference above.

As shown best in FIG. 9, connector block (300) of suction attachment (260) is affixed to a proximal portion of cannula assembly (270), such that the proximal portion extends through connector block (300) to expose open proximal end (272) through a proximal face (302) of connector block (300). Connector block (300) houses a pair of electrical connectors (304a, 304b) that are exposed through proximal face (302) and are positioned on either lateral side of open proximal end (272). In the present version, electrical connector (304a) is electrically coupled with navigation sensor (292) of sensor assembly (290), while electrical connector (304b) is electrically coupled with an EEPROM (306) housed within connector block (300), as described below. Electrical connector (304a) may be coupled with navigation sensor (292) via a wire (not shown) similar to communication wire (196) described above. Such a wire may extend longitudinally along cannula assembly (270) through a pathway defined between an outer surface of interior suction tube (282) and an inner surface of external sheath (280). Each electrical connector (304a, 304b) is configured to electrically couple with a respective electrical connector (236a, 236b) of handle assembly (220) when suction attachment (260) is coupled with handle assembly (220).

In the present version, handle assembly electrical connectors (236a, 236b) are shown in the form of female connectors comprising electrical sockets, while suction attachment electrical connectors (304a, 304b) are shown in the form of male connectors comprising pins configured to be received within the sockets. It will be appreciated that various other suitable arrangements of electrical connectors (236a, 236b, 304a, 304b) may be employed in other versions. For instance, each of handle assembly (220) and connector block (300) may comprise one female electrical connector and one male electrical connector. Alternatively, as described below, each of handle assembly (220) and connector block (300) may have a single electrical connector that encompasses the same number of pins and sockets otherwise encompassed by electrical connectors (236a, 236b, 304a, 304b). To that end, each electrical (236a, 236b, 304a, 304b) may comprise any suitable quantity and arrangement of pins or sockets. By way of example only, electrical connectors (236a, 236b, 304a, 304b) may comprise connectors by Mill-Max, Mfg. Corp. of Oyster Bay, New York.

As shown in FIG. 9, connector block (300) of suction attachment (260) additionally houses a second EEPROM (306) operable to store data relating to suction attachment (260). Such data may include a serial number; a bend angle of bent portion (276) of cannula assembly (270); a distance of sensor assembly (290) from connector block (300) or another reference point; other physical characteristics of suction attachment (260); and/or previous usage of suction attachment (260). In the present example, attachment EEPROM (306) is electrically coupled with electrical connector (304b) of connector block (300). Accordingly, when electrical connector (304b) is coupled with electrical connector (236b) of handle assembly (220), attachment EEPROM (306) is placed in communication with PCB board (238), which in turn is configured to communicate with processor (18) of navigation system (10) via electrical connector (234), as described above. In some alternative versions of suction instrument (210), handle assembly (220) and suction attachment (260) may each include a single electrical connector having electrical contacts that transmit electrical signals for both navigation sensor (292) and attachment EEPROM (306). In such versions, the mixed signals received by the handle assembly (220) may be separated through processing with a signal filter device (not shown) arranged within or externally of handle assembly (220).

In some instances, it may be desirable to discard or sanitize suction attachment (260) after a maximum period of use (e.g., after one or more uses). In that regard, and as described above, attachment EEPROM (306) may be operable track and store data relating to usage of suction attachment (260). In some versions, attachment EEPROM (306) may be configured to direct a notification feature to provide an indication to the operator that the maximum period of use has been reached, such that suction attachment (260) should be sanitized or discarded without further use. Alternatively, or in addition, attachment EEPROM (306) may be configured to direct a disabling feature to prevent or otherwise limit further use of suction attachment (260) once the maximum period of use has been reached. Such a notification feature and disabling feature may be integrated into a portion of suction instrument (210) or be provided separately from suction instrument (210). It will be appreciated that similar use notification and/or use disabling features may be provided in connection with handle assembly (220) and handle EEPROM (240). For instance, and by way of example only, suction attachment (260) may be subject to two or more uses before requisite sanitization or disposal thereof; and handle assembly (220) may be subject to 100 or more uses before requisite sanitization or disposal thereof. Additionally, attachment EEPROM (306) and/or handle EEPROM (240) may include one or more safety features coded within their software that prevent an end user from overriding the disabling feature(s) or the notification feature (s).

In some versions, handle assembly (220) or a processor external of handle assembly (22), such as processor (18) of navigation system (10), may be suitably configured to prevent usage of a non-recognized attachment with handle assembly (220). For instance, handle assembly PCB board (238) or navigation system processor (18) may be configured to identify a serial number stored by attachment EEPROM (306); and cross-reference the identified serial number with a database of acceptable serial numbers. If the identified serial number is not included within the database, or if the distal attachment has no serial number stored at all (e.g., where an EEPROM (306) is entirely omitted from the attachment), handle assembly (220), suction attachment (260), and/or suction source (80) may be automatically disabled by a disabling feature.

It will be appreciated that additional EEPROMS may be provided throughout various other portions of suction instrument (210), coupling unit (120), and/or IGS navigation system (10) as desired. For instance, a first additional EEPROM may be provided in cable (126) of coupling unit (120); and may be configured to store data relating to coupling unit (120). A second additional EEPROM may be provided in a coupling device (e.g., a "dongle") that couples coupling unit (120) with console (20) of IGS navigation system (10); and may be configured to amplify signals transmitted between coupling unit (120) and console (20).

As shown in FIGS. 6A-7 and 8, connector block (300) of suction attachment (260) further includes a coupling feature in the form of a pair of prong-like arms (308) projecting proximally from opposed lateral sides of proximal face (302). Each arm (308) is configured to slide longitudinally into a respective one of recessed channels (242) of handle assembly body (222). Such engagement of arms (308) with recessed channels (242) promotes alignment of suction attachment electrical connectors (304a, 304b) with handle assembly electrical connectors (236a, 236b). Engagement of arms (308) with recessed channels (242) also promotes coaxial alignment of open proximal end (272) of cannula assembly (270) with the open distal end of suction passage (230) of handle assembly (220), such that suction passage (230) may fluidly communicate with suction lumen (284) upon full engagement of suction attachment (260) with handle assembly (220). While handle assembly (220) and connector block (300) of the present version are shown having coupling features in the form of recessed channels (242) and arms (308), it will be appreciated that various other types of coupling features may be employed in other versions.

As shown in FIGS. 6A-7 and 10, full engagement of suction attachment (260) with handle assembly (220) operates to electrically couple suction attachment electrical connectors (236a, 236b) with handle assembly electrical connectors (236a, 236b), and simultaneously fluidly couple suction lumen (284) of suction attachment (260) with suction passage (230) of handle assembly. As shown in FIG. 10, open proximal end (272) of cannula assembly (270), which includes a proximal end of suction tube (282), projects slightly into handle assembly body (222) to establish the fluid communication between suction lumen (284) and suction passage (230). Accordingly, suction may be communicated from suction source (80), through suction passage (230), to suction lumen (284) for suctioning liquids and/or debris through open distal end (274) of cannula assembly (270) from a surgical site at which open distal end (274) is positioned by the operator. The operator may control the amount of suction communicated to open distal end (274) by selectively covering vent opening (232) in the manner described above. Simultaneously, navigation sensor (292) is configured to interact with the electromagnetic field generated by field generators (16) about patient's head (H) (see FIG. 1) to generate electrical signals that are communicated proximally through cannula assembly (270), handle assembly (220), and coupling unit (120) to console (20) of IGS navigation system (10). In response to receiving these signals, processor (18) may then determine and display via display (24) a 3-dimensional spatial location of open distal end (274) relative to the anatomy of patient (P).

In some versions, connector block (300) and/or handle assembly body (222) of suction instrument (210) may include a locking feature (not shown) operable to enhance the mechanical coupling between handle assembly (220) and connector block (300) by releasably retaining arms (308) within recessed channels (242) when connector block (300) and handle assembly (220) are fully pressed together. Such a locking feature may be configured to permit separation of connector block (300) from handle assembly body (222) only in response to an action taken by the operator to intentionally separate suction attachment (260) from handle assembly (220). The locking feature may be further configured to maintain distal face (223) of handle assembly body (222) in sufficient approximation with proximal face (302) of suction attachment (260) that prevents liquids from contacting and shorting electrical connectors (236a, 236b), and prevents air, liquids, and other debris from leaking through the interface between suction lumen (284) and suction passage (230) (see FIG. 10). Such a locking feature may comprise one or more latches, detents, magnets, or other suitable mechanisms readily apparent to those of ordinary skill in the art in view of the teachings herein. The locking feature may be integrated into arms (308) and recessed channels (242), or on other portions of connector block (300) and handle assembly body (222).

Additionally, in some versions, handle assembly (220) and/or suction attachment (260) may include one or more electrical seals (not shown) configured to prevent liquids from contacting and shorting electrical connectors (236a, 236b, 304a, 304b). Such electrical seals may encircle one or more of electrical connectors (236a, 236b) at distal face (223) of handle assembly body (222) and/or one or more of electrical connectors (304a, 304b) proximal face (302) of connector block (300). Such seals may comprise any suitable material, such as foam or rubber, configured to resiliently compress between faces (223, 302) when suction attachment (260) is fully attached to handle assembly (220). Furthermore, suction instrument (210) may include a suction seal (not shown) configured to prevent leakage of air, liquid, and debris through the junction between suction lumen (284) of cannula assembly (270) and suction passage (230) of handle assembly (220). Such a suction seal may be provided in the form of an o-ring seal provided at open proximal end (272) of cannula assembly (270) or within the open distal end of suction passage (230). It will be appreciated that various other forms of seals and gasket-like structures may be provided at the interface between handle assembly (220) and suction attachment (260) to prevent leakage of the suction flow path and to protect electrical connectors (236a, 236b, 304a, 304b) from shorting.

Figure 11:
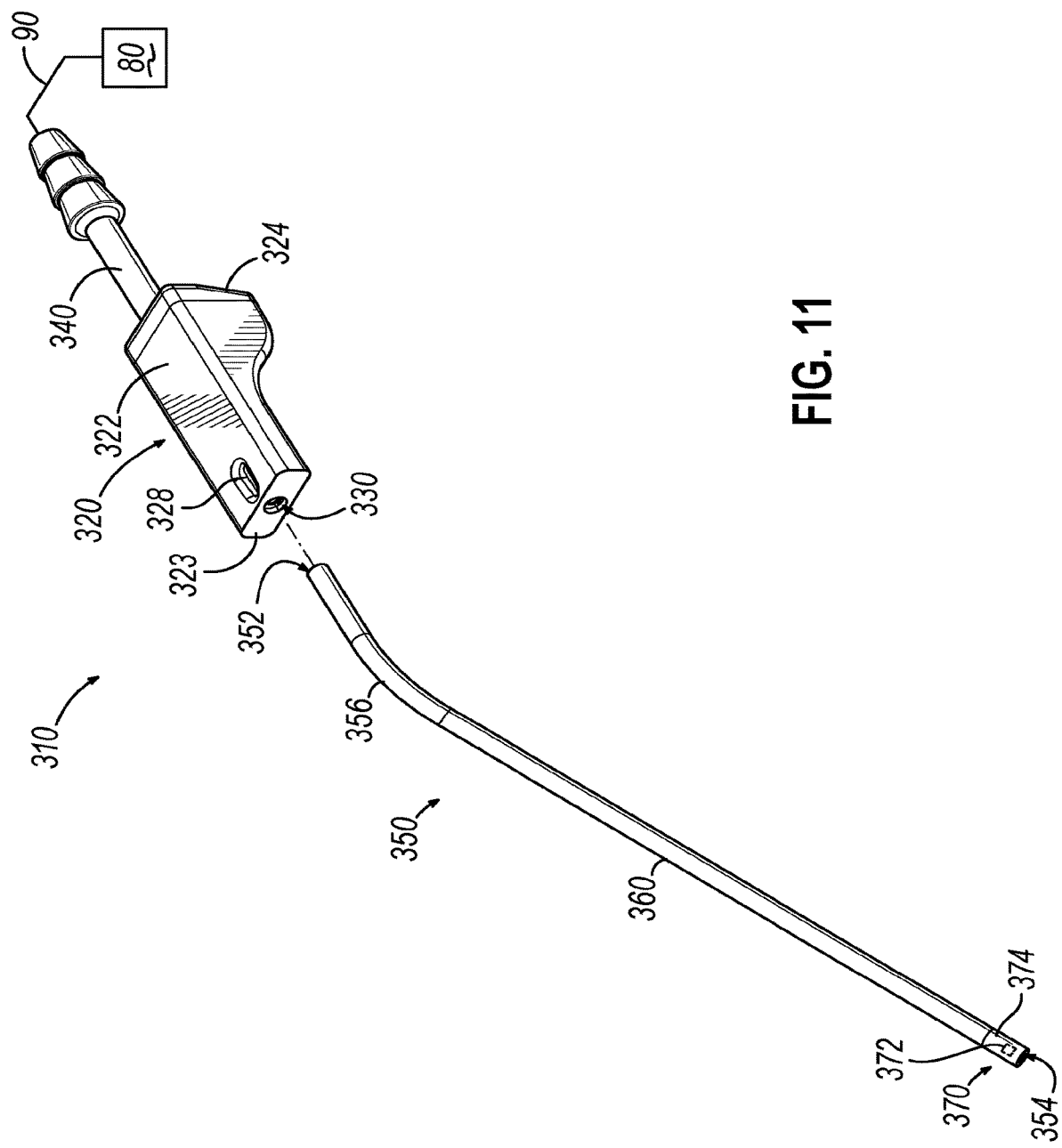
FIG. 11 depicts a perspective view of another exemplary suction instrument suitable for use with the navigation system of FIG. 1, showing a distal suction attachment decoupled from a proximal handle assembly.
Figure 12:
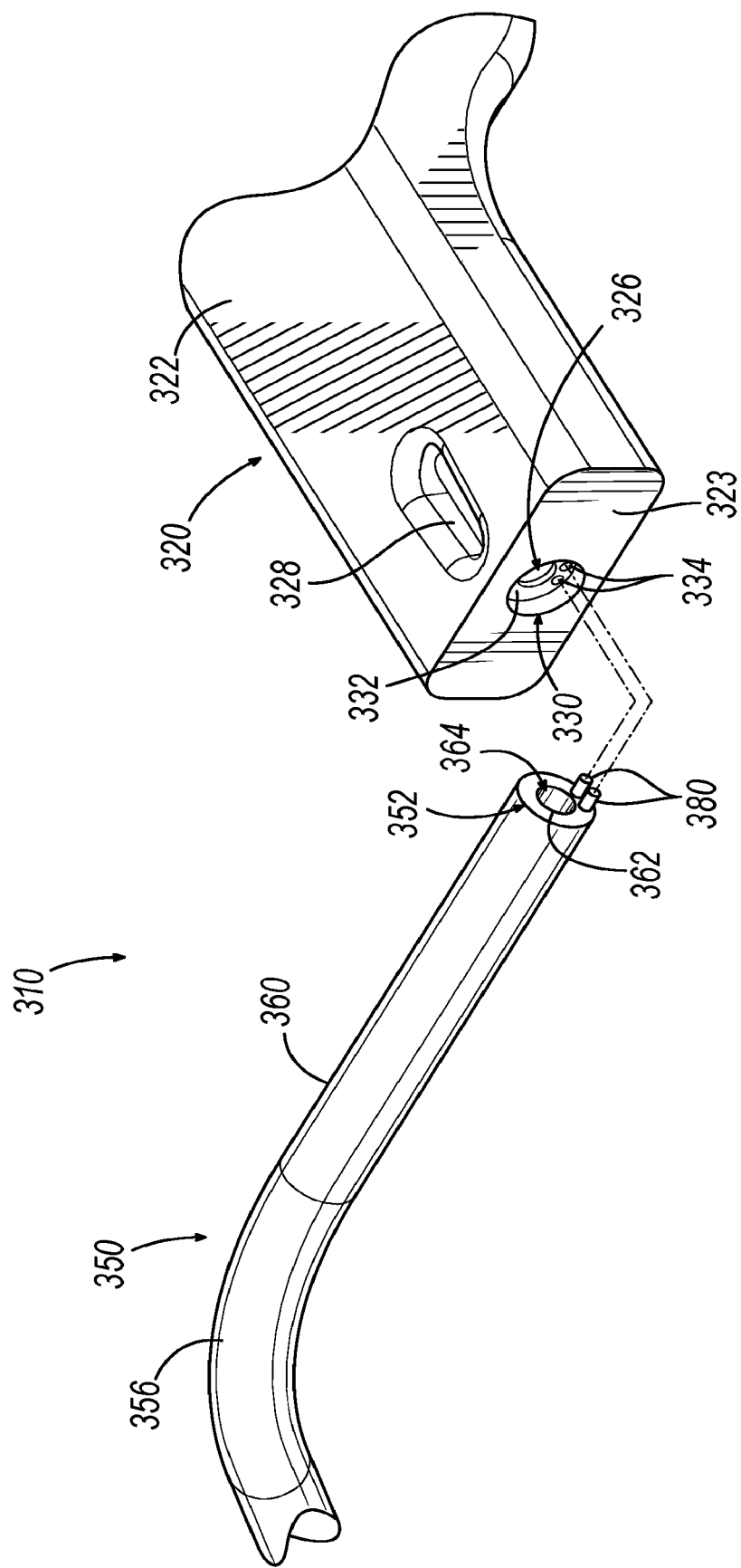
FIG. 12 depicts an enlarged perspective view of coupling portions of the proximal handle assembly and the distal suction attachment of the suction instrument of FIG. 11.

B. Navigable Suction Instrument Having Detachable Cannula Assembly with Integrated Electrical Contacts In some instances, it may be desirable to omit connector block (300) from suction instrument (210) to provide a more size efficient variation of suction attachment (260). FIGS. 11-12 show an exemplary alternative navigation suction instrument (310) having a handle assembly (320) and a detachable cannula assembly (350) with a proximal end (352) suitably configured to releasably couple directly with handle assembly (320). Handle assembly (320) is similar to handle assembly (220) described above in that handle assembly (320) includes a body (322) defining an interior cavity (not shown), and a proximal cap (324) coupled to a proximal end of body (322). A suction passage (326) extends longitudinally through body (322) and fluidly communicates with a vent opening (328) formed in an upper surface of body (322). A suction conduit port (340) extends proximally from proximal cap (324) and is configured to couple with a suction conduit (90) to thereby fluidly couple suction passage (326) of handle assembly (320) with suction source (80).

A distal face (323) of handle assembly body (322) includes an attachment port (330) configured to releasably receive proximal end (352) of cannula assembly (350), as described below. Attachment port (330) of the present example includes an annular recessed shoulder (332) that defines an open distal end of suction passage (326), and a pair of electrical contacts in the form of electrical sockets (334) provided in recessed shoulder (332). Electrical sockets (334) are electrically coupled with one or more electrical components housed within handle assembly body (322), which may comprise components similar to coupling connector (234), PCB board (238), and handle EEPROM (240)

of handle assembly (220) described above. It will be appreciated that various suitable types of electrical contacts other than sockets (334) may be provided on recessed shoulder (332) or the sidewall that encircles recessed shoulder (332) in other versions of handle assembly (320).

Detachable cannula assembly (350) is similar to cannula assembly (270) described above in that detachable cannula assembly (350) extends between open proximal end (352) and an open distal end (354), with a bent portion (356) arranged therebetween. Additionally, detachable cannula assembly (350) includes an external sheath (360), an internal suction tube (362) defining a suction lumen (364), a sensor assembly (370) arranged at open distal end (354) and having a navigation sensor (372), and a distal cap (374) that circumferentially encloses sensor assembly (370). These components may be similar to the corresponding components of cannula assembly (270) described above.

Open proximal end (352) of detachable cannula assembly (350) includes an integrated pair of electrical contacts in the form of pins (380) that project proximally. Electrical pins (380) are electrically coupled with navigation sensor (372) and optionally also with an EEPROM (not shown) housed within or otherwise coupled to a portion of cannula assembly (350) and which may be similar to attachment EEPROM (306) described above. It will be appreciated that various suitable types of electrical contacts other than pins (380) may be provided at open proximal end (352) in other versions. For instance, open proximal end (352) may include one or more electrical contact sockets configured to receive one or more electrical contact pins projecting from recessed shoulder (332) of handle assembly (320).

Open proximal end (352) of detachable cannula assembly (350) is configured to be releasably received within attachment port (330) of handle assembly (320) to securely couple cannula assembly (350) with handle assembly (320) mechanically and electrically. In particular, a proximal face of open proximal end (352) abuts recessed shoulder (332) within attachment port (330) so that suction lumen (364) of cannula assembly (350) fluidly couples with suction passage (326) of handle assembly (320); and so that electrical pins (380) of cannula assembly (350) are received within and electrically couple with electrical sockets (334) of handle assembly (320). Once fully assembled, suction instrument (310) is operable in connection with IGS navigation system (10) in a manner similar to suction instruments (110, 210) described above.

Though not shown, handle assembly (320) and/or detachable cannula assembly (350) of suction instrument (310) may further include one or more resilient seals operable to prevent leakage of air, fluids, or debris from the junction between suction lumen (364) and suction passage (326). Such seals may also be operable to prevent fluids from contacting and shorting electrical contacts (334, 380). Additionally, handle assembly (320) and/or detachable cannula assembly (350) may further include one or more releasable locking features (e.g., latches, detents, magnets, etc.) operable to enhance the mechanical coupling between handle assembly (320) and detachable cannula assembly (350).

While handle assemblies (220, 320) of suction instruments (210, 310) are shown and described herein in connection with suction attachments (260, 350), it will be appreciated that handle assemblies (220, 320) may be used interchangeably with various other types of surgical attachments having proximal ends suitably configured to releasably couple with handle assemblies (220, 320). By way of example only, such alternative attachments may incorporate, in whole or in part, any one or more of the devices disclosed in U.S. Pub. No. 2018/0085174, entitled "Suction Device for Use in Image-Guided Sinus Medical Procedure," published Mar. 29, 2018, now abandoned; U.S. App. No. 62/658,688, entitled "Curette with Navigation Sensor," filed Mar. 17, 2018; U.S. application Ser. No. 15/795,473, entitled "Tissue Shaving Instrument," filed Oct. 27, 2017, issued as U.S. Pat. No. 10,631,890 on Apr. 28, 2020; U.S. application Ser. No. 15/830,205, entitled "Dilation Instrument with Navigation and Distally Located Force Sensor," filed Dec. 4, 2017, issued as U.S. Pat. No. 10,861,046 on Dec. 15, 2020; U.S. application Ser. No. 15/839,274, entitled "Tissue Shaving Instrument with Navigation Sensor," filed Dec. 12, 2017, issued as U.S. Pat. No. 10,959,785 on Mar. 30, 2021; U.S. application Ser. No. 15/852,470, entitled "Dilation Instrument with Guide Catheter Type Sensor," filed Dec. 22, 2017, now abandoned; U.S. application Ser. No. 16/002,016, entitled "Endoscope with Integral Navigation Sensor," filed Jun. 7, 2018, published as U.S. Pub. No. 2019/0374129 on Dec. 12, 2019; U.S. App. No. 62/765,168, entitled "Endoscope with Anatomy Elevation Assembly," filed Aug. 17, 2018; U.S. App. No. 62/741,594, entitled "Hollow Tube Surgical Instrument with Single Axis Sensor," filed Oct. 5, 2018; U.S. App. No. 62/741,614, entitled "Dilation Instrument with Malleable Guide and Dilation Catheter with Integral Position Sensor," filed Oct. 5, 2018; or U.S. App. No. 62/741,778, entitled "Pointer Instrument with Malleable Shaft and Integral Position Sensor," filed Oct. 5, 2018; the disclosures of these references being incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a proximal end; (b) a distal end, wherein the distal end is configured to be positioned within or adjacent to an anatomical passageway of a patient; (c) a suction lumen extending between the proximal and distal ends, wherein the suction lumen is configured to provide suction at the distal end; (d) a navigation sensor disposed along a portion of the suction lumen, wherein the navigation sensor is operable to generate an electrical signal corresponding to a location of the portion within the patient; and (e) a coupling feature disposed at the proximal end, wherein the coupling feature is configured to releasably couple the proximal end with a body.

Example 2

The surgical instrument of Example 1, further comprising a suction tube, wherein the suction tube defines the suction lumen.

Example 3

The surgical instrument of any of the preceding Examples, wherein the navigation sensor is disposed at the distal end.

Example 4

The surgical instrument of any of the preceding Examples, wherein the navigation sensor comprises an electromagnetic sensor.

Example 5

The surgical instrument of Example 4, wherein the electromagnetic sensor comprises an electrically conductive coil.

Example 6

The surgical instrument of any of the preceding Examples, further comprising an electrical connector disposed at the proximal end, wherein the electrical connector is electrically coupled with the navigation sensor.

Example 7

The surgical instrument of any of the preceding Examples, further comprising an EEPROM, wherein the EEPROM is operable to store data relating to the suction instrument.

Example 8

The surgical instrument of any of the preceding Examples, further comprising a connector block disposed at the proximal end, wherein the suction lumen extends distally relative to the connector block.

Example 9

The surgical instrument of Example 8, wherein the coupling feature comprises at least one of a projection or a recess provided by the connector block.

Example 10

The surgical instrument of any of the preceding Examples, wherein the coupling feature comprises a first coupling feature, wherein the suction instrument further comprises a body having a second coupling feature configured to releasably engage the first coupling feature to thereby releasably couple the suction lumen with the body.

Example 11

The surgical instrument of Example 10, wherein the body includes a passageway having a proximal end configured to fluidly couple with a suction source, and a distal end configured to fluidly couple with the suction lumen when the first coupling feature is engaged with the second coupling feature.

Example 12

The surgical instrument of any of Examples 10 through 11, wherein the body includes a vent opening that fluidly communicates with the passageway and the suction lumen, wherein the vent opening is configured to be selectively closed to communicate suction from the suction source to the suction lumen.

Example 13

The surgical instrument of any of Examples 10 through 12, further comprising: (a) a first electrical connector disposed at a proximal end of the suction lumen, wherein the first electrical connector is electrically coupled with the navigation sensor, and (b) a second electrical connector disposed at a distal end of the body, wherein the second electrical connector is configured to communicate with a processor, wherein the first and second electrical connectors are configured to electrical couple together when the suction lumen is coupled with the body to thereby transmit the electrical signal from the navigation sensor to the processor.

Example 14

The surgical instrument of Examples 10 through 13, further comprising a connector block disposed at a proximal end of the suction lumen, wherein the connector block provides the first coupling feature.

Example 15

The surgical instrument of Examples 10 through 14, further comprising: (a) a first EEPROM housed within the connector block, wherein the first EEPROM is operable to store data relating to at least one of the connector block or the suction lumen, and (b) a second EEPROM housed within the body, wherein the second EEPROM is operable to store data relating to the body.

Example 16

A surgical instrument comprising: (a) a body comprising: (i) a proximal end configured to couple with a suction source, and (ii) a distal end configured to releasably couple with an attachable member having a suction lumen, wherein a distal end of the attachable member is configured to be positioned within or adjacent to an anatomical passageway of a patient, wherein the body is configured to be gripped by a user for manipulating the attachable member relative to the patient; (b) a passageway extending through the body, wherein the passageway comprises: (i) a proximal end configured to fluidly couple with the suction source, and (ii) a distal end configured to fluidly couple with the suction lumen of the attachable member, wherein the suction passageway is configured to communicate suction from the suction source to the suction lumen; and (c) a first electrical connector arranged at the distal end of the body, wherein the first electrical connector is configured to releasably couple with a second electrical connector of the attachable member to receive an electrical signal that corresponds to a location of the attachable member within the patient.

Example 17

The surgical instrument of Example 16, further comprising a first coupling feature arranged at the distal end of the body, wherein the first coupling feature is configured to releasably couple with a second coupling feature of the attachable member, wherein the first coupling feature is further configured to promote alignment of the first electrical connector with the second electrical connector during attachment of the attachable member to the body.

Example 18

The surgical instrument of any of Examples 16 through 17, further comprising an EEPROM housed within the body, wherein the EEPROM is operable to store data relating to the body.

Example 19

A surgical instrument comprising: (a) a body, wherein the body has a first coupling feature; and (b) a cannula assembly configured to extend distally from the body, wherein the cannula assembly comprises: (i) a suction tube having an open distal end configured to provide suction within or adjacent to an anatomical passageway of a patient, (ii) a navigation sensor disposed along a portion of the suction tube, wherein the navigation sensor is operable to generate an electrical signal corresponding to a location of the portion within the patient, and (iii) a second coupling feature disposed at a proximal end of the suction tube, wherein the second coupling feature is configured to releasably engage the first coupling feature to thereby couple the suction tube with the body.

Example 20

The surgical instrument of Example 19, wherein the body includes a first electrical connector configured to electrically couple with a processor, wherein the cannula assembly includes a second electrical connector electrically coupled with the navigation sensor, wherein the first and second electrical connectors are configured to releasably couple together to transmit the electrical signal from the navigation sensor to the processor.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. In some instances, the instrument may be placed in a reprocessing tray (e.g., a metal bin or basket) and then cleaned in a surgical instrument washer. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, steam, hydrogen peroxide vapor (e.g., via a STERRAD sterilization system by Advanced Sterilization Products of Irvine, California), and/or using any other suitable systems or techniques.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A method comprising:
   releasably coupling a proximal end of a cannula assembly to an attachment port of a handle assembly to thereby form a surgical instrument, wherein the proximal end of the cannula assembly comprises electrical pins config- ured to releasably couple with electrical sockets provided in an annular recessed shoulder of the attachment port;
positioning a distal end of a cannula assembly within or adjacent to an anatomical passageway of a patient;
generating electrical signals via a navigation sensor, wherein the navigation sensor is disposed along a portion of the cannula assembly, and the electrical signals indicate a position of the navigation sensor in three-dimensional space; and
providing suction to the distal end of the cannula assembly through a suction lumen of the cannula assembly, the suction lumen being in fluid communication with the distal end of the cannula assembly, the handle assembly providing suction to the suction lumen.

2. The method of claim 1, wherein the handle assembly having-comprises a distal end defining an attachment port, the cannula assembly including a cannula tube with a proximal end, and releasably coupling the proximal end of the cannula assembly to the handle assembly comprises inserting the proximal end of the cannula tube into the attachment port.

3. The method of claim 1, wherein the navigation sensor is disposed at the distal end of the cannula assembly, and the electrical signals indicate a position of the distal end of the cannula assembly in three-dimensional space.

4. The method of claim 1, wherein the navigation sensor comprises an electromagnetic sensor, and the method further comprises generating an electromagnetic field, the electrical signals being generated in response to a presence of the navigation sensor within the electromagnetic field.

5. The method of claim 4, wherein the electromagnetic sensor comprises an electrically conductive coil, and the electrically conductive coil generates the electrical signals.

6. The method of claim 1, wherein the cannula assembly further comprises a first electrical connector disposed at the proximal end of the cannula assembly, the handle assembly comprises a second electrical connector, and releasably coupling the proximal end of the cannula assembly to the handle assembly comprises coupling the first electrical connector with the second electrical connector.

7. The method of claim 1, wherein the surgical instrument comprises an electrically erasable programmable read-only memory (EEPROM), and the method further comprises one or both of:
storing data in the EEPROM; or
reading data from the EEPROM.

8. The method of claim 1, wherein releasably coupling the proximal end of the cannula assembly to the attachment port of the handle assembly comprises inserting the proximal end into the annular recessed shoulder.

9. The method of claim 1, wherein the cannula assembly including comprises a cannula tube with a proximal end, the proximal end of the cannula tube comprises a first set of electrical coupling features, a distal portion of the handle assembly comprises a second set of electrical coupling features, and releasably coupling the proximal end of the cannula assembly to the handle assembly further comprises engaging the first set of electrical coupling features with the second set of electrical coupling features.

10. The method of claim 1, wherein the handle assembly comprises a vent opening, and providing suction to the distal end of the cannula assembly comprises covering the vent opening.

11. The method of claim 10, further comprising uncovering the vent opening to relieve suction to the distal end of the cannula assembly.

12. The method of claim 11, wherein the cannula assembly further comprises an EEPROM, releasably coupling the proximal end of a cannula assembly to the handle assembly comprises establishing an electrical connection between the cannula assembly and the handle assembly, and the method further comprises:
communicating data from the EEPROM to the handle assembly via the electrical connection; and
communicating the electrical signals from the navigation sensor to the handle assembly via the electrical connection.

13. A surgical instrument comprising a body, the body comprising:
a proximal end configured to couple with a suction source;
a distal end, the distal end comprising:
recessed channels configured to releasably couple with retaining arms of an attachable member having a suction lumen, and
a first electrical connector, the first electrical connector being configured to releasably couple with a second electrical connector of the attachable member to receive an electrical signal that corresponds to a location of the attachable member within a three-dimensional space, and the recessed channels being further configured to promote alignment of the first electrical connector with the second electrical connector during attachment of the attachable member to the body; and
a passageway extending through the body, the passageway comprising:
a proximal end configured to fluidly couple with the suction source, and
a distal end configured to fluidly couple and align with the suction lumen of the attachable member via the releasable coupling of the recessed channels and the retaining arms, the passageway being configured to communicate suction from the suction source to the suction lumen.

14. The surgical instrument of claim 13, further comprising the attachable member, the attachable member comprising a cannula defining the suction lumen.

15. The surgical instrument of claim 14, further comprising one or both of the following:
a first electrically erasable programmable read-only memory (EEPROM) housed within the attachable member, the first EEPROM being operable to store data relating to the suction lumen; or
a second EEPROM housed within the body, the second EEPROM being operable to store data relating to the body.

16. The surgical instrument of claim 13, wherein the recessed channels have a length, the length being approximately half as long as the attachable member.

17. The surgical instrument of claim 13, wherein the first electrical connector is symmetrically oriented around the distal end of the passageway.

18. A method of using a surgical instrument, the method comprising:
forming the surgical instrument by releasably coupling pins that longitudinally extend from a proximal end surface of a cannula assembly to sockets in an attachment port of a handle assembly, wherein releasably coupling the pins to the sockets comprises forming an electrical connection;
generating electrical signals via a navigation sensor, wherein the navigation sensor is disposed along a portion of the cannula assembly, the electrical signals indicate a position of the navigation sensor in three-dimensional space, and the handle assembly receives the electrical signals;

communicating the electrical signals to a processor to thereby indicate the position of the navigation sensor to an operator; and providing suction to a distal end of the cannula assembly through a suction lumen of the cannula assembly via the handle assembly, the suction lumen being in fluid communication with the distal end of the cannula assembly.

19. The method of claim 18, wherein the attachment port comprises an annular recessed shoulder, and the sockets are provided on the annular recessed shoulder.

20. The method of claim 18, wherein the attachment port comprises an annular recessed shoulder, and the sockets are provided on a sidewall that encircles the annular recessed shoulder.

* * * * *